United States Patent [19]

Schiller et al.

[11] 4,145,255
[45] Mar. 20, 1979

[54] METHOD AND DEVICE FOR THE DETECTION OF PHENOL AND RELATED COMPOUNDS

[75] Inventors: James C. Fletcher, Administrator of the National Aeronautics and Space Administration, with respect to an invention of Julian G. Schiller; Chung C. Liu, both of Pittsburgh, Pa.

[73] Assignee: The United States of America as represented by the Administrator of the National Aeronautics and Space Administration, Washington, D.C.

[21] Appl. No.: 772,167

[22] Filed: Feb. 25, 1977

[51] Int. Cl.² ............................ C12B 1/00; C12K 1/10
[52] U.S. Cl. ............................. 195/103.5 R; 195/127; 204/1 T; 204/195 B
[58] Field of Search ....................... 195/127, 103.5 R; 204/1 E, 195 B

[56] References Cited
U.S. PATENT DOCUMENTS 3,403,081  9/1968  Rohrback et al. ............... 195/127 X

OTHER PUBLICATIONS

Thomas E. Barman, Enzyme Handbook, vol. 1, Springer-Verlag; 1969, pp. 226 and 227.

Primary Examiner—Raymond N. Jones
Assistant Examiner—Robert J. Warden
Attorney, Agent, or Firm—N. T. Musial; J. R. Manning; J. A. Mackin

[57] ABSTRACT

Phenol or a phenol related compound is detected in an electrochemical cell comprising a cathodic compartment containing a cathode in an electrolyte solution containing ferrocyanide ion and an anodic compartment containing an anode formed by coating a gel containing a phenol or phenol related compound oxidizing enzyme onto the conductive substrate of said anode immersed into an electrolyte solution containing ferrocyanide ion into which pure oxygen is passed; means for maintaining a conductive relationship between anodic and cathodic compartments; and means connected to said anode and cathode for measuring the potential of the oxidation of said phenol or related compound.

11 Claims, 3 Drawing Figures

METHOD AND DEVICE FOR THE DETECTION OF PHENOL AND RELATED COMPOUNDS

ORIGIN OF THE INVENTION

The invention described herein was made in the performance of work under a NASA contract and is subject to the provisions of Section 305 of the National Aeronautics and Space Act of 1958, Public Law 85–568 (72 stat. 435, 45 USC 2457).

BACKGROUND OF THE INVENTION

1. Field of the Invention

The present invention relates to an electrochemical cell for the detection of phenol and related compounds. More particularly, the present invention relates to the electrochemical detection of phenol and related compounds in a cell containing an anode on whose surface is coated an immobilized enzyme.

2. Description of the Prior Art

Electrochemical procedures have been developed in the past for the detection of a variety of organic molecules including sugars, such as glucose, fructose and sucrose; alcohols such as methyl alcohol, ethyl alcohol and the like; glycols such as ethylene glycol and the like. In one technique as disclosed in U.S. Pat. No. 3,647,641, a reactant sensor is employed for the electrochemical analysis of a variety of organic molecules which employ a gas diffusion cathode and an anode. Both electrodes are immersed in a solution containing an electrolyte and the substance to be detected, and are conductively attached to an ammeter. The cathode which is employed in the technique is a gas diffusion electrode which is a porous carbon substrate with a silver catalyst which has been wet proofed and has an impervious mask thereon except for that portion of the electrode which is exposed to oxygen or air. The anode is a conductive substrate coated with a catalytic metal such as platinum, palladium or the like. In the use of the device, the organic material to be detected is catalytically ozidized at the anode and oxygen is reduced at the gas diffusion cathode, thereby setting up a current which is measured by the ammeter and which is limited by the concentration of organic material at the electrode surface. However, the technique shown by the reference is an amperometric method, and its does not show or suggest a method of potentiometrically detecting phenol and related compounds in solution.

A need, therefore, continues to exist for a method of potentiometrically measuring phenol and related compounds.

SUMMARY OF THE INVENTION

Accordingly, one object of the present invention is to provide an electrochemical cell for the detection of phenol and related compounds.

Another object of the present invention is to provide a method for potentiometrically measuring the enzymic oxidation of phenol and related compounds at the anode of an electrochemical cell.

Yet another object of the invention is to provide an anode for the electrochemical detection of phenol and related compounds having a gel immobilized, oxidative enzyme supported thereon.

Briefly, these objects and other objects of the present invention as hereinafter will become more readily apparent can be attained by a method of detecting phenol or a phenol related compound in an electrochemical cell comprising a cathodic compartment containing a cathode in an electrolyte solution containing ferrocyanide ion; an anodic compartment containing an anode formed by coating a gel containing a phenol or phenol related compound oxidizing enzyme onto the conductive substrate of said anode immersed into an electrolyte solution containing ferrocyanide ion; means for maintaining a conductive relationship between anodic and cathodic compartments; and means connected to said anode and cathode for measuring the potential of the oxidation of said phenol or related compound.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

The discovery of the present invention provides a method by which phenol and related compounds can now be selectively oxidized and detected potentiometrically in an electrochemical cell. Thus, the method is useful for the determination of phenolic pollutants in industrial effluents and surface waters, and the like. In the method an anode coated with a gel immobilized oxidative enzyme and a cathode are each placed in an electrolyte solution, and the potential of the cell is measured by a potentiometer connected to the electrodes.

It is known that biochemically, phenol can be oxidized by oxygen in the presence of the phenolase, tyrosinase (E.C.1.14.18.1) to 1,2-dihydroxybenzene and then to o-benzoquinone. If ferrous ions are present during the oxidation reaction such as derived from added potassium ferrocyanide, the ferrous ions are oxidized to ferric ions with the simultaneous reduction of o-benzoquinone. to 1,2-dihydroxybenzene as shown as follows:

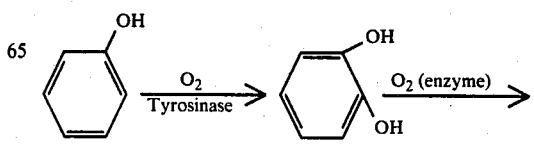

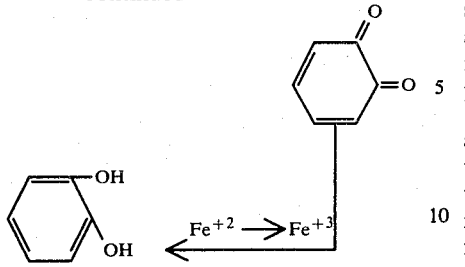

The accumulation of ferric ions produced by the reduction of o-benzoquinone to dihydroxybenzene can be measured spectrometrically at 420 nm and in this manner tyrosinase activity is measured.

When the enzyme catalyzed oxidation reaction of dihydroxybenzene to o-benzoquinone and the reduction of benzoquinone back to dihydroxybenzene with the concomitant oxidation of ferrous ion to ferric ion are in equilibrium, a Nernstian potential would be developed for the reactions. In the system if ferrous ions are in excess (relative to ferric ions) and the hydrogen ion concentration is negligible by buffering the solution, then the combined Nerstian potential can be used as an indication of the ratio of activities of 1,2-dihydroxybenzene relative to o-benzoquinone and ferrous ion relative to ferric ion. Thus, the determination of the activity of phenol is based on the Nernstian potential. Moreover, if ferrous ions are present in the reaction solution, they function to facilitate the establishment of equilibrium between the o-benzoquinone and 1,2-dihydroxybenzene as well as facilitate electron transfer and balance in the reactions.

Figure 1:
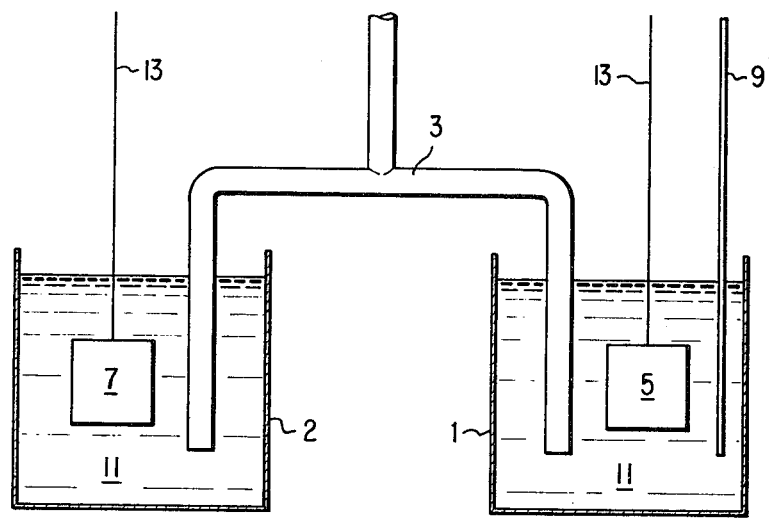
FIG. 1 shows an embodiment of the electrochemical cell of the present invention.

A better understanding of the invention can be attained by referring to the embodiment of the invention shows in FIG. 1 which shows an electrochemical cell containing an anode compartment 1 and a cathode compartment 2 conductively linked by salt bridge 3. The anode compartment is provided with an immobilized enzyme grid anode 5, while the cathode compartment is provided with cathode or reference electrode 7. The anode compartment is supplied with oxygen inlet conduit 9 whose open end is positioned beneath the surface of the electrolyte solution 11 in the anode compartment in order to maintain a sufficient level of oxygen concentration in the solution. Each electrode is connected to the terminals of a potentiometer (not shown) by conductive leads 13.

The anode employed in the electrochemical cell is constructed in a manner such that the selective oxidation of phenol and related compounds occurs at the electrode and is constructed such that a phenol oxidizing enzyme such as tyrosinase is immobilized in a gel coating on the conductive substrate of the anode. The anode substrate can be of any convenient physical configuration such as a wire, thin sheet or screen, preferably a screen. Suitable conductive materials from which the anode substrate can be formed include the noble metals such a platinum, palladium, silver, and the like, as well as nickel and the like. The functioning anode of the present invention is prepared by coating the substrate with a permeable gel containing the enzyme. Normally, the permeable gel coated on the anode contains from 30 to 300 enzyme units. Experiments have shown that when the amount of entrapped enzyme is reduced to between 3 to 30 units, significant decreases in the open-circuit potential values were observed, and at enzyme loadings of 3 units per grid, little or no response was obtained from the system when phenol was added at any concentration. Suitable gel forming materials which are compatible with the enzyme include polyacrylamide, collagen, zein, agar, and the like.

In the preparation of the enzyme containing anode any method can be used which results in the immoiization of the phenolase enzyme in one of the above mentioned gel forming materials. In a preferred embodiment aqueous solutions of enzyme, riboflavin, persulfate, polyacrylamide and bisacrylamide cross-linking agent containing a buffer such as phosphate sufficient to buffer at a pH of 6.5-8.0 are prepared. Riboflavin functions as a cofactor for enzyme in the anode. If the amount of cofactor present is too small, the gel will not properly form about the anode. If the amount of cofactor is to high, the enzyme will not be sufficiently dissolved in the casting solution. The amount of persulfate ion relative to enzyme in the membrane is not critical, and the amount of cross-linking agent used need only be that amount sufficient to provide a stable gel about the conductive substrate of the anode. Amounts of each of the solutions are combined such that a satisfactory gel forming solution is formed. A mold containing an appropriately shaped electrode is filled with the deoxygenated solution and polymerization is conducted by exposing the filled mold to a source of excitation such as ultraviolet light. After polymerization is complete, the enzyme electrodes are removed from the mold and can be stored in the phosphate buffer solution used above to form the casting solution at a temperature below room temperature, preferably about 6° C.

The cathode which is coupled with the enzyme coated anode of the invention can be any suitable conductive electrode. Oxygen in solution is reduced at the cathode. Usually the normal concentration of oxygen in solution is sufficient for the reduction reaction at the cathode. However, if desired, oxygen or an oxygen-inert gas mixture can be passed into the solution of the cathode compartment in the manner accomplished in the anode compartment. The cathode can be of any convenient size and shape such as a wire, thin film, screen or the like. Suitable metals from which the cathode can be formed include the noble metals such as platinum, palladium, silver and the like, as well as nickel and the like.

In order to set up the electrochemical cell each electrode is placed within a compartment containing an electrolyte solution, and oxygen is introduced into the solution of the anode compartment. Oxygen introduction is most conveniently accomplished by bubbling oxygen into the electrolyte solution, although any other manner of introducing oxygen can be employed. By bubbling oxygen into the anode solution sufficient concentration levels of oxygen can be achieved in the solution for participation in the oxidation of phenol or a related compound in the anode compartment. The best results are obtained when 100% oxygen is bubbled into the anode electrolyte solution at a flow rate sufficient to achieve oxidation of the phenol or phenol related compound. A preferred flow rate is about 60 ml/min. However, oxygen-inert gas mixtures can also be employed in which oxygen is present in an amount as low as about 4% as demonstrated by the data in FIG. 3.

The electrolyte solution employed in each compartment is not critical and any electrolyte solution normally employed in electrochemical cells can be used.

Thus, the solution in each compartment of th cell can contain such inorganic salts such as the chloride, bromide, nitrate, sulfate and the like salts of the alkali metals. Other solutions which can be conveniently employed as electrolyte solutions include buffer solutions. Any buffer with a capacity to buffer the solution at a pH of at least 6.5, i.e. 6.5–8.0, may be used with the provision that the buffer does not detrimentally affect the immobilized enzyme. Suitable buffer solutions include phosphate salt solutions. The temperature of the solution during measurement is not critical, but should be controlled over a range such that the enzyme is not deactivated. A preferred temperature range is 15° C to 30° C. The electroylyte solutions in which the anode and cathode are immersed must contain $K_4Fe(CN)_6$ in a concentration which increases the magnitude of the potentimetric response of the anode. It is only necessary that the amount of $Fe(CN)_6^{-4}$ present be sufficient to provide an amount of $Fe^{+3}$ ion in excess of the concentration of phenol or phenol related compound in solution. A preferred concentration of $K_4Fe(cN)_6$ in solution is about 0.02 M. As explained earlier, it is believed that the ferrocyanide ion functions as a source of $Fe^{+2}$ ions in solution which are oxidized in solution to $Fe^{+3}$ by the oxidation product resulting from the oxidation of the phenolic substrate with enzyme. The accumulation of $Fe^{+3}$ ions is believed responsible for the development of the open circuit potential.

In the method of the present invention a sample containing or believed to contain phenol or phenol related compound is placed in the anodic compartment. The phenolase enzyme immobilized on the anode catalyzes the oxidation of the phenol to orthobenzoquinone in a two electron oxidation reaction which is measured by a potentiometer connected to the leads of both electrodes. Other suitable phenol compounds include cresol, catechol, L-dihydroxyphenylalanine, resorcinol, orcinol, hydroquinone, 2-methylhydroquinone, phenyl-4-catechol, 3,4-dihydrocinnamic acid, chlorogenic acid, 4-hydroxyphenol acetic acid, 2,4,6-trichlorophenol, 2-aminophenol, α-naphthol, pyrogallol, gallic acid, shikimic acid, quinic acid, phloroglucinol, 3-hydroxybenzoic acid, 4-hydroxybenzoic acid, 3,4-dihydroxybenzoic acid, 2,3-dihydroxybenzoic acid, 3,4-dihydroxybenzalehyde, 4-hydroxybenzaldehyde, and the like. The concentration of the phenol which can be detected by the present method ranges from $3.0 \times 10^{-7}M$ to $1.0 \times 10^4M$. The type of potentiometer used with the device of the present invention is not critical and any type of potentiometer normally used in electrochemical measurements can be employed.

The apparatus shown in FIG. 1 is one embodiment of the device of the present invention in which a salt bridge 3 is used to provide a conductive link between the anodic and cathodic compartments 1 and 2 of the electrochemical cell. The type of salt bridge used in such an apparatus is not critical and any of the conventional types of salt bridges used in electrochemical measurements can be employed such as KCl salt bridge.

Another embodiment of the electrochemical cell of the present invention is similar to that of FIG. 1 with the only difference being that instead of dividing the cell into anode and cathode compartments conductively linked by a salt bridge, the entire cell is in a single container wherein both anode and reference electrodes are immersed in the same electrolyte solution.

Another possible cell configuration is similar to the embodiment discussed above except that the container is divided into two compartments by a semipermeable conductive membrame such as a glass frit. One of the two electrodes is then immersed in the electrolyte solution in one of the compartments, while the other electrode is immersed in the solution in the other compartment.

Having generally described this invention, a further understanding can be obtained by reference to certain specific examples which are provided herein for purposes of illustration only and are not intended to be limiting unless otherwise specified.

EXAMPLE 1

Referring to the apparatus of FIG. 1, an electrochemical cell having separated anodic and cathodic compartments and conductively joined by a KCl salt bridge was constructed. Into the anodic and cathodic compartments were placed equal amounts (40 ml) of 0.25 M potassium phosphate buffer at a pH of 6.5 containing 0.02 M $K_4Fe(CN)_6$. Into the cathodic compartment was placed an electrode of a 2.0 × 2.0 cm platinum screen, and the electrode was attached to a terminal of a potentiometer.

An anode was formed by coating a platinum screen of a basket weave design (0.11 × 1.5 × 1.5 cm) with a polyacrylamide gel containing 140 units of phenolase enzyme (E.C. 1.14.18.1). The polyacrylamide gel containing the enzyme was prepared as described by Hicks et al Anal. Chem., 38, 726 (1966), in which 6.20 grams of an acrylamide monomer and 1.55 g of [N,N-methylenebis(acrylamide)] cross-linking agent were contained in 100 ml of the gel. The anode was formed by casting the deoxygenated gel into a glass mold (0.12 × 2.0 × 7.0 cm) containing the base platinum screen. Polymerization was initiated by subjecting the gel to a 15 watt fluorescent bulb at a distance of 5 cm. Thirty minutes after the polmerization appeared complete, the enzyme grids were removed from the mold and stored in 0.25 M potassium phosphate buffer (pH 6.5) at 6° C. No observable change in the mechanical or physical appearance of the enzyme grids was detected.

Figure 2:
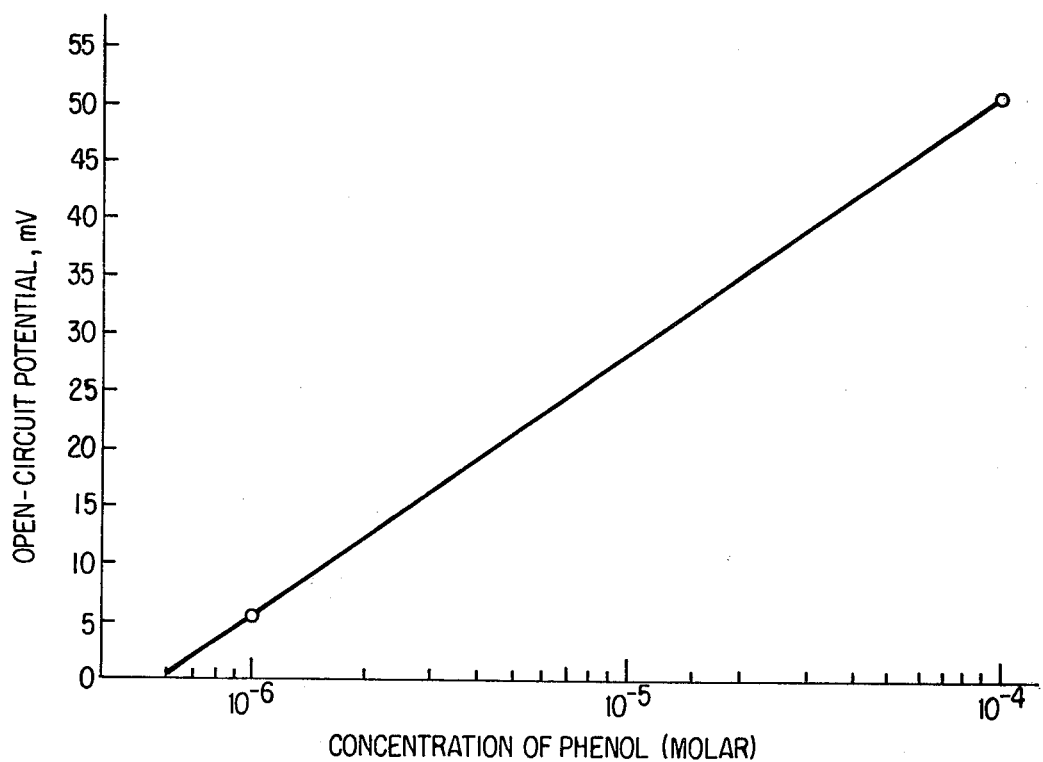
FIG. 2 shows the open-circuit potential of the electrochemical cell of FIG. 1 for the phenolase catalyzed oxidation of phenol in a solution containing $K_4Fe(CN)_6$ at the anode of the cell.

The prepared anode was then placed in the anode compartment and attached by a lead to the potentiometer. Oxygen was admitted into the anode compartment. After a steady state potential was reached, after about 5–10 minutes, which was not zero potential, samples of phenol were added to the anode compartment. (The baseline of the measurement however, was set at zero volts prior to addition of phenol or the phenol related compound.) FIG. 2 shows the response of the cell with respect to phenol concentration for a series of phenol concentrations in the anode compartment at 22° C.

A control experiment was also conducted in the same manner described aboved except that the platinum grid of the anode was not coated with a gel containing enzyme. The results of the experiments were that no response was obtained when phenol was added to the anode compartment.

EXAMPLE 2

An enzyme grid was prepared by forming a solution of the enzyme tyrosinase, bisacrylamide, riboflavin and persulfate in in 0.1M phosphate buffer at a pH of 6.5 and then deoxygenating the solution. A 1.5 × 1.5 × 0.11 cm piece of basket woven platinum screen was then placed inside a glass mold (0.12 × 2.0 ×7.0 cm) which was filed with the deoxygenated gel solution. Polymerization of the solution was initiated by exposing the mold to radiation within 5 cm of a 15 watt fluorescent bulb. Thirty minutes after polymerization, the grids were removed from the mold and then stored in 0.25 M phosphate buffer (pH 6.5) at 6° C. Several enzyme grids prepared by this technique contained 300 ± 15 enzyme units per grid. Platinum wire (10 mil diameter and 5 cm length) was spot welded onto the grid of each electrode. In the preparation of a complete cell, another platinum screen with similar dimensions and lead wire was used as the reference electrode.

An electrochemical cell was formed by using two 50 ml glass beakers as half-cell chambers which were conductively linked by a saturated potassium salt bridge. The bridge was formed of 5 mm (ID) glass tubing and refilled daily before use. The ends of the bridge were sealed with medium porosity sintered glass filters. Each half cell was filled with 40 ml of 0.25 M phoshate buffer, pH 6.5 and optionally 0.02 M potassium ferrocyanide was added. Into each half cell either oxygen or oxygen-nitrogen mixtures were bubbled through the solution via Pasteur pipettes. The gas flow rate was maintain at 60 ml/min. in each half-cell. At the beginning of each experiment, gas was bubbled through each half-cell for seven minutes before a phenol containing sample was added to the anode compartment. The gas was continuously bubbled through the solutions for the duration of each experiment. The oxygen content of the solutions was measured with a clinical blood gas analyzer (Instrumentation Laboratory Model 132). The equilibrated solution had an oxygen concentration of 100%, 25% or 4%. The buffered solution in both half-cells were changed prior to each measurement. Freshly prepared concentrated phenol solutions (0.4 ml) were added to the anode half-cell chamber at the start of each experiment.

The open-circuit potentials of the complete cell were measured with a Hewlett-Packard Model 7702 B recorder with a Model 8803A high gain DC preamplifier. The recording system had a minimum input of one megohm. Usually, the recorder was operated at a sensitivity of 2,000 $\mu$v/division and a chart speed of 1 mm/sec., and baseline drift was minimized by adjusting the zero suppression. If any residual baseline drift occurred, it was measured for two minutes before addition of phenol and was substracted when appropriate from the measured open-circuit potential. The immobilized enzyme cell described above containing 300 enzyme units and equilibrated with 100% oxygen was used in a comparative experiment with essentially the same cell except the anode compartment contained only a platimum screen electrode and the electrolyte solution contained 300 enzyme units of free enzyme. The results of the experiment indicate that the open circuit potential for the immobilized enzyme is more rapid and reaches it equilibrium value after only three minutes. For the free enzyme system, however, the open circuit potential approaches its equilibrium value after about 10 minutes.

To further correlate the above experiments, the same measurements with the immobilized membrane electrode system and the free enzyme system were conducted in the presence of ferrous ions, and the change in absorbance at 420 nm was determined for the immobilized membrane system versus the free enzyme system. (Each measurement system contained 0.02M $K_4Fe(CN)_6$ which was gassed with 100% oxygen and contained phenol at a concentration of $1 \times 10^{-4}$ M. The data obtained revealed that the change in absorbance for the free enzyme containing system is more rapid than the change in absorbance for the immobilized membrane system. In the case of the immobilized system, diffusional resistance keeps the reaction product, i.e. ferric ion, at low concentration in the surrounding medium. Thus, the change in absorbance in the microenvironment of the gel containing the immobilized membrane is even more rapid and extensive than that found for the free enzyme. Consequently, a more rapid response in the open circuit potential is observed for the immobilized enzyme.

Figure 3:
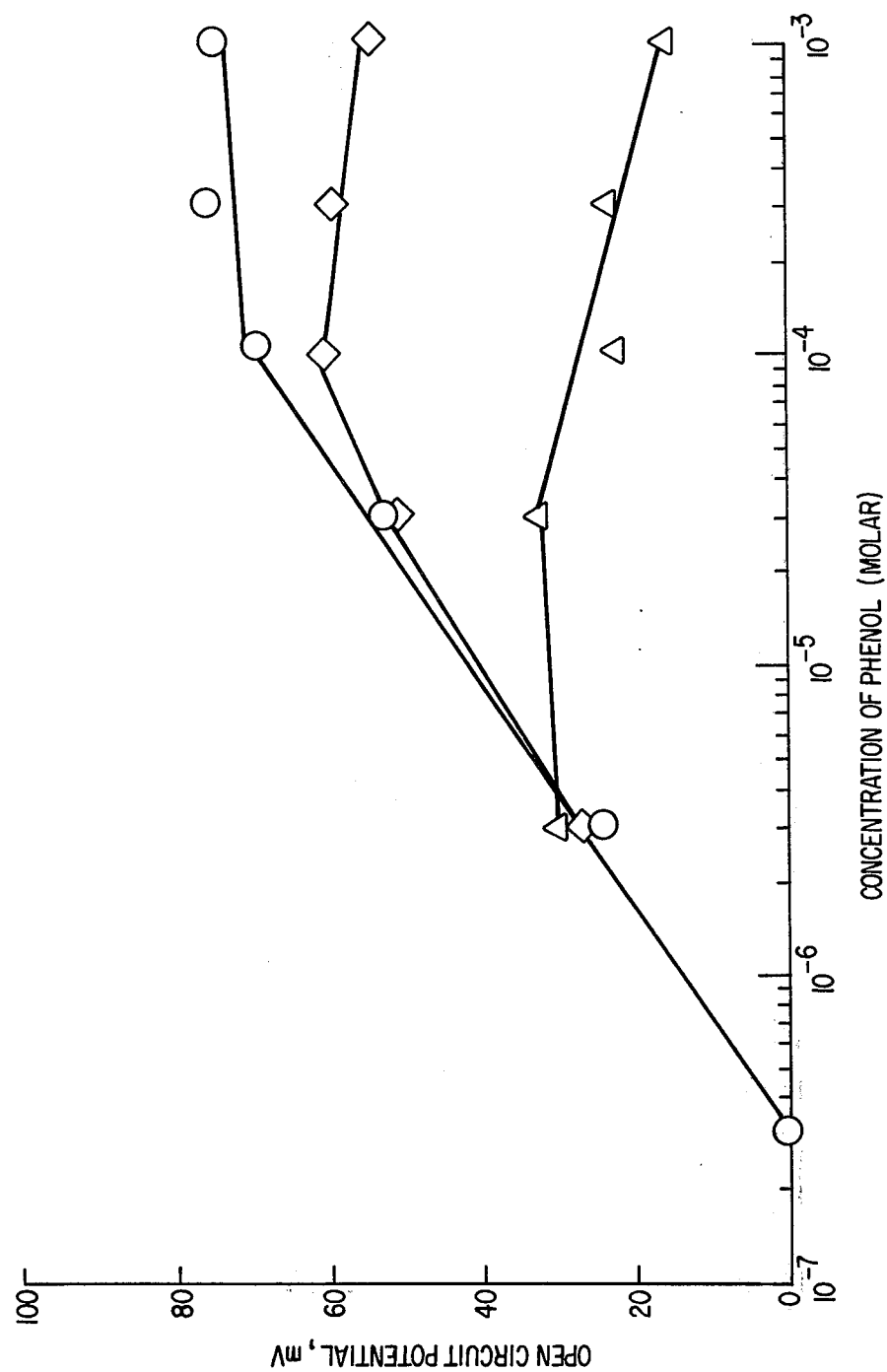
FIG. 3 is a graph of open circuit potential versus phenol concentration showing the dependence of the open circuit potential on the oxygen concentration of the oxygen containing gas admitted into the half cell containing the enzyme electrode at a 100% oxygen tension at the reference electrode.

In another set of experiments the dependence of the immobilized enzyme membrane system of the present invention on oxygen concentration was demonstrated. Oxygen, an oxygen nitrogen mixture (25% $O_2$) and nitrogen (4% $O_2$) were used to provide different $O_2$ concentrations in the anode compartment. The oxygen concentration was maintained at 100% in the cathode compartment or half-cell containing the reference electrode. FIG. 3 shows the results obtained wherein the symbol ● represents the situation of 100% $O_2$ concentration in the anode half-cell ◇ represents the situation of 25% $O_2$ in the anode half-cell and ▶ represents the situation of 4% $O_2$ in the anode half-cell. The graph shows that the best results are obtained at 100% $O_2$ concentration.

A set of control experiments was also conducted in which acrylamide gel electrodes were used which did not contain tyrosinase cast about a platinum screen. The potentiometric measurements obtained indicated no potential response in the absence of enzyme.

Having now fully described the invention, it will be apparent to one of ordinary skill in the art that many changes and modifications can be made thereto without departing from the spirit or scope of the invention as set forth herein.

What is claimed as new and intended to be secured by Letters Patent is:

1. An electrochemical cell for the detection of phenol and phenol related compounds which comprises:
   a cathode compartment containing a cathode in an electrolyte solution containing ferrocyanide ion;
   an anodic compartment containing an anode formed by coating a gel containing a phenol or phenol related compound oxidizing enzyme onto the conductive substrate of said anode immersed into an electrolyte solution containing ferrocyanide ion;
   means for directing oxygen into said electrolyte solution in said anodic compartment;
   means for maintaining a conductive relationship between anodic and cathodic compartments; and
   means connected to said anode and cathode for measuring the potential of the oxidation of said phenol or phenol related compound.

2. The electrochemical cell of claim 1, wherein said oxidizing enzyme is phenolase (E.C.1.14.18.1).

3. The electrochemical cell of claim 1, wherein said means for maintaining a conductive relationship between said anodic and cathodic compartments is a salt bridge.

4. The electrochemical cell of claim 1, wherein said conductive substrate of said anode is a member selected from the group consisting of platinum, palladium, silver and nickel.

5. The electrochemical cell of claim 1, wherein said anode is a platinum screen upon which is coated a polyacrylamide gel containing phenoloxidase.

6. The electrochemical cell of claim 1, wherein said anode contains from 30–300 units of phenolase.

7. The electrochemical cell of claim 1, wherein said anode and cathode compartments are a single container containing said electrolyte solution into which oxygen is passed.

8. A method for electrochemically measuring the oxidation of phenol and phenol related compounds which comprises:

adding a sample containing phenol or a phenol related compound to the anode compartment of an electrochemical cell provided with an electrolyte containing ferryocyanide ion solution equipped with an anode of a conductive substrate upon which is coated a gel containing a phenol or phenol related compound oxidizing enzyme, said anode compartment being in conductive contact with a cathode compartment containing a cathode in the same electrolyte solution of the anode compartment containing ferrodyanide ion, said anode and said cathode being conductively connected to a potential measuring means, and directing oxygen into said electrolyte in said anode compartment then, measuring the potential of the oxidation of said phenol or phenol related compound at the anode of said cell.

9. The method of claim 8, wherein said phenol or related compound is selected from the group consisting of phenol, cresol, resorcinol, catechol, orcinol, L-hydroxyphenylalanine, hydroquinone, 2-methylhydroquinone, phenyl-4-catechol, 3,4-dihydrocinnamic acid, chlorogenic acid, 4-hydroxyphenol acetic acid, 2,4,6-trichlorophenol, 2-aminophenol, α-naphthol, pyrogallol, gallic acid, shikimic acid, quinic acid, phloroglucinol, 3-hydroxybenzoic acid, 4-hydroxybenzoic acid, 3,4-dihydroxybenzoic acid, 2,3-dihydroxybenzoic acid, 3,4-dihydroxybenzaldehyde, and 4-hydroxybenzaldehyde.

10. The method of claim 8, wherein said gel is selected from the group consisting of polyacrylamide, collagen, zein and agar.

11. The method of claim 8, wherein said enzyme is phenolase (E.C.1.14.18.1).